United States Patent [19]

Johnson et al.

[11] 4,002,738
[45] Jan. 11, 1977

[54] TREATMENT OF SPECIFIED NEOPLASIAS

[75] Inventors: Edwin Samuel Johnson, Antioch; John Hunter Seely, Lake Forest, both of Ill.

[73] Assignee: Abbott Laboratories, North Chicago, Ill.

[22] Filed: May 30, 1975

[21] Appl. No.: 582,319

[52] U.S. Cl. .............................................. 424/177
[51] Int. Cl.² ........................................ A61K 37/02
[58] Field of Search .................................... 424/177

*Primary Examiner*—Jerome D. Goldberg
*Attorney, Agent, or Firm*—Paul D. Burgauer; Robert L. Niblack

[57] ABSTRACT

A series of nonapeptide amides has been found which, upon administration at daily dosages of from about 1–200 µg/kg to warm-blooded animals, cause regression and subsequent elimination of certain tumors without causing adverse effects on healthy tissues.

7 Claims, No Drawings

TREATMENT OF SPECIFIED NEOPLASIAS

DETAILED DESCRIPTION OF THE INVENTION

For a number of years there has been a search for substances that, upon administration to warm-blooded animals, will cause the regression and/or elimination of tumors without causing substantial adverse effect to healthy tissue of the host.

It has now been found that a series of closely related peptides have the ability to interfere with the metabolism of certain tumors to the point of drastically impairing their cell growth which, in turn, leads to tumor regression and oftentimes, to the elimination of the tumor all together.

The principal object of the present invention is, therefore, to provide a treatment for warm-blooded animals that carry one or more active tumors or neoplasias; it is a more particular object of this invention to provide a chemical treatment for warm-blooded animals afflicted with certain tumor growth which reduces the size of said tumor without adverse effect to the host.

These and other objects are accomplished by administering to a warm-blooded animal, carrying a growing mammary or DMBA-inducible tumor, a sufficient daily dose of a nonapeptide of the formula

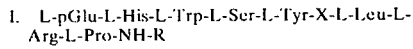

wherein X denotes the optically active D-form of an aminoacid of the formula —NH—CHR'—CO— with R' being a linear or branched carbon chain of 1 – 4 carbon atoms and wherein R is lower alkyl. The term "lower alkyl" is used to include alkyl groups containing between 1 and 7 carbon atoms. The divalent radical X may be best illustrated by the D-leucyl, D-alanyl, D-valyl or D-isoleucyl moieties.

While the described treatment may be effective against other tumors as well, it is primarily directed to the regressive effect it has on tumors of the female reproductive organs, particularly tumors of the ovaries, the uterus and the female breast.

In a general embodiment, the above nonapeptide is administered to a warm-blooded animal carrying a tumor of the above type at a parenteral dose of between 1 and 200 μg/kg/day as a single daily dose or divided into 2–4 daily doses of the correspondingly smaller amounts. Where oral administration is desired, the dose range is between 2 and 500 μg/kg/day and can easily be exceeded since the compound of formula I does not show any toxic effects at oral doses 100 mg/kg or more. The above reference to "parenteral" is intended to include all routes of administration other than oral; it is particularly directed to intramuscular, subcutaneous, intravenous by injection or infusion, intra-vaginal, by suppository, by nasal drops, etc. For these formulations, solutions of I at a concentration of 5–100 μg/ml in 0.9% saline provide an excellent dosage form. If desired, small amounts of albumin may be added to prevent adsorption of I to the glass container in which this dosage form is prepared or stored.

The compound of formula I is highly water-soluble; it can be stored for essentially indefinite periods of time as a solid or as a solution in water or saline. Of course, where desired, buffers such as tris(hydroxymethyl)aminomethane or other pharmaceutically acceptable additives may be included in the solutions before storage or before use.

For oral preparations, any number of pharmaceutical forms can be used, e.g., syrups, elixirs, suspensions or the compound can be processed into wafers, pills, tablets and the like. However, since the dosage required is extremely small, the usual tableting methods require the use of fillers and other excipients to prepare tablets of manageable size. In a preferred embodiment, the oral dosage form consists of a tablet containing between 0.1 and 5.0 mg. of the above peptide per tablet. Such tablets can be coated in the usual fashion, preferably using a readily soluble coating material, e.g., sugar, etc. or the above amount can be incorporated into gelatin capsules which promptly dissolve upon introduction into the stomach. In any event, the usual flavoring and coloring agents can be used without effect on the active peptide so incorporated.

Tablets of this type are prepared in the usual fashion by compounding the active ingredient with starch, granulating the mixture and, after adding the necessary fillers, flavoring agents, lubricants, etc., the mixture is slugged and passed through a 30-mesh screen. The thoroughly blended mixture is then compressed into tablets of desired hardness with the usual punch, preferably to make bisected tablets for easier b.i.d. administration.

In order to show the preparation and use of the compounds of the present invention, reference is made to the following examples which, however, are not intended to limit the invention in any respect. For the purpose of this description, the terms Neoplasia and tumor are used interchangeably.

EXAMPLE 1

Proline carrying as a blocking group the t-butyloxycarbonyl substituent (elsewhere herein referred to as Boc-) on the amino group is esterified by combining it with a chloromethylated divinylbenzene-styrene copolymer (marketed by Bio-Rad as Merrifield resin) containing 2% of cross linking, using the method described by Stewart, et al. in "SOLID PHASE PEPTIDE SYNTHESIS", (published in 1969 by Freeman & Company), San Francisco, (page 1). In this manner, a resin is produced which by hydrolysis and aminoacid analysis shows to contain 0.47 millimoles of proline/g. of resin. In an automatic synthesizer developed according to the previously cited Merrifield apparatus, 4.6 g. of this resin/aminoacid material is used for the synthesis of the desired nonapeptide. Each N-blocked aminoacid is added in a three-fold access and allowed to couple to the existing aminoacid-resin ester in the usual coupling cycle. The coupling reaction is carried out for 4.5 hours with continuous shaking and the reaction is subsequently washed six times with methanol-chloroform 1:2 for 1.5 minutes each and 4 times with ethanol for 1.5 minutes each. In each instance, a total volume of 48 milliliters is used and the drain time after shaking usually is about 1.5 minutes.

After coupling, the mixture is washed four times for 1.5 minutes each with dioxane, twice with 4N hydrochloric acid/dioxane for 5 minutes and 25 minutes, respectively, five times with dioxane for 1.5 minutes each, three times with ethanol for 1.5 minutes each, three times with chloroform for 1.5 minutes each, three times with 10% triethylamine/chloroform for 1.5 minutes each, four times with chloroform for 1.5 minutes each and six times with dichloromethane for 1.5 minutes each. Ordinarily the solvent used for the coupling reaction is dichloromethane or, when the solubility of the blocked aminoacid is low, a mixture of dichloromethane and dimethylformamide. Coupling is effected by the addition of a solution of dicyclohexylcarbodiimide in dichloromethane at a 2.9 fold excess.

The sequence used for deprotection, neutralization and coupling of the next aminoacid is done in a fully automatic system as described above. In this manner, the peptide is assembled using in turn Boc-Arg(Tos), Boc-Leu, Boc-D-Leu, Boc-Tyr(Cl$_2$Bzl), Boc-Ser(Bzl), Boc-Trp, Boc-His(DNP), and pGlu wherein all aminoacids are in the L-form except in the leucine so designated.

The resin is removed from the vessel and suspended in 200 ml. of 5% triethylamine/methanol and 100 ml. of distilled ethylamine is added thereto. After 24 hours, the resin is removed by filtration and the solution evaporated to yield a solid. The solid is taken up in glacial acetic acid and applied to a 3 × 50 cm. column of silica gel equilibrated with 5% methanol/chloroform.

The column is eluted with 5% methanol in chloroform until all traces of N-ethyl dinitroaniline, the yellow by-product of the histidine protecting group DNP is removed. The eluant is then changed to 33% methanol/chloroform and fractions of about 30 ml. each are collected. The compound is located by thin-layer chromatography of aliquots of the fractions (Silica gel G. 33% MeOH/CHCl$_3$, Cl$_2$/tolidine spray). The fractions containing the product are pooled and evaporated to give a solid which is precipitated from methanol with ether. This tri-protected nonapeptide (protective groups at Ser, Tyr and Arg) is thus obtained in an amount of 1.69 g., representing an overall yield of 43% of theory.

A 250 mg. sample of the above is placed in a hydrogen fluoride reaction vessel with 250 mg. of anisole and about 5 ml. of anhydrous hydrogen fluoride is distilled into it. After 1 hour at 0° C., the hydrogen fluoride is removed in vacuo, and the residue is taken up in 1% acetic acid. This solution is extracted with ether, and the aqueous phase applied to a 1 × 30 cm. column of a highly basic ion exchange resin (marketed by Bio-Rad as AGl × 2 resin) in the acetate form. The product is eluted with 0.1 N acetic acid and localized using thin-layer chromatography (CHCl$_3$/MeOH/32% HOAc: 120/90/40, Silica gel G., Cl$_2$/tolidine). The product bearing solution is lyophilized, rechromatographed on a Sephadex G-25 (marketed by Pharmacia of Uppsala, Sweden) column. The product eluted is collected and lyophilized to yield a fluffy white solid $[a]_D^{25} = -31.7°$ (c = 1, 1% HOAc) in a 25% overall yield. Analysis shows the expected ratio of all desired aminoacids assembled in the above fashion.

When in the above synthesis, the Boc-D-leucine is replaced by the correspondingly protected α-aminobutyric acid, alanine, isoleucine or valine, the above synthesis proceeds in the same fashion, again in all instances, using the automatic synthesizer described above.

EXAMPLE 2

A female rat that had developed a spontaneous growth in the right lateral mammary region was given b.i.d. 10 μg. of the compound of formula I (R' = isobutyl; R = ethyl). Before the start of these subcutaneous injections with the aqueous solution of the test compound (1 ml contained 20 μg. of the above compound and 9 mg of NaCl), the tumor had a diameter of 3 cm. On days 5, 9 and 20 of the treatment, the diameter had reduced to 2 cm., 0.5 cm. and finally to an undetectable size, respectively. On day 9, a biopsy was performed and the tumor was identified as adenocarcinoma of the mammary gland.

Treatment was stopped after 20 days and the animal was observed periodically. Tumor growth reappeared in the same area with rapid growth observed on day 65 (counted from original treatment beginning). On day 66, the tumor had a diameter of 4 cm. and a depth of 2 cm., with ulceration in the center. Treatment with the above regimen was started again. The tumor regressed again and on day 93, its diameter was 1.2 cm. and its depth was 0.4 cm.

Further observation of the animal showed swelling of the area of the tumor upon surgically cleaning and skin closing. However, the tumor remained dormant until day 147 (54 days following the last treatment), when significant growing resumed.

EXAMPLE 3

In a group of 3 female, 50-day old rats, tumors were induced by intragastric feeding of 20 mg of 7,12-dimethylbenzanthracene (DMBA) in 2 ml. of sesame oil. The animals developed tumors within 10–12 weeks. All animals were maintained on normal rations for 100 days following the DMBA administration, at which time treatment with the compound of formula I (R = ethyl; R' = isobutyl) was started at a b.i.d. regimen Monday through Friday with a single dose on Saturday, the compound being subcutaneously administered as a 0.2% (wt/vol.) solution in isotonic saline.

The first animal carrying 4 tumors of volumes of 5.5, 3, 1 and 1 cc. respectively, was given the above regimen with 10 μg per dose. After 2 weeks, two of the tumor volumes were found to be 1 cc; the other two tumors were of immeasurable volumes.

In the second animal carrying 3 tumors, each dose contained only 5 μg of the drug. One tumor was seemingly unaffected by the drug; the others showed a tumor volume regression from 4 to 2 cc. and from 3 to 1¼ cc., respectively.

The third animal had developed 5 tumors, measuring 6.5, 3.5, 1.5, 0.5 and 0.5 cc. respectively. After treatment with 2.5 μg. per dose of the test drug, these tumors were reduced to 1.5, 3.0, 0.5, 0.2 and >0.0 cc. in that sequence.

Although the above demonstrations involve only the use of the compound of formula I wherein X is the D-leucyl moiety and R is ethyl, all analogs included in that formula show substantially the same in vivo results. It does appear, however, that the compounds wherein R is ethyl are preferred. The compounds wherein X is another D-aminoacid than isoleucine are prepared in the same manner as described in Example 1, except for replacing the D-Boc-leucine with the corresponding D-Boc-iso-leucine, D-Boc-alanine, D-Boc-valine, D-Boc-norleucine or D-Boc-α-aminobutyric acid. In these instances, R' of the above moiety —NH—CHR'—CO— contain 1–4 carbon atoms; they are preferred, although R' moieties with 5–7 carbon atoms also show desirable tumor controls and regressions.

As demonstrated above, the treatment with the compounds of formula I produces drastic regression of mammary tumors and those tumors induced or inducible by chemical carcinogens. Both of these types of tumors in rodents have been shown to be reliable models for tumors in other warm-blooded animals. Thus, the above defined narrow class of compounds can be used for the amelioration of these tumors, the eventual elimination of these tumors upon prolonged treatment as well as the extension of the host's survival rate. Since these compounds have essentially no toxicity even in doses of 100 mg/kg, and since the doses to be used for successful treatment in animals are in the µg/kg levels, the therapeutic index of the compounds is extremely high. This makes the above treatment an important and unexpected discovery and valuable addition to the field of tumor treatments.

We claim:

1. The method of reducing the size of a mammary or DMBA-inducible tumor in a warm-blooded animal by administering to said animal an effective daily amount to reduce the size of said tumor of a nonapeptide of the formula L-pGlu-L-His-L-Trp-L-Ser-L-Tyr-X-L-Leu-L-Arg-L-Pro-NH-R wherein X denotes the optically active D-form of an aminoacid of the formula —NH—CHR'—CO— with R' being a linear or branched carbon chain of 1 – 4 carbon atoms and wherein R is lower alkyl.

2. The method of claim 1 wherein R' is isobutyl and R is ethyl.

3. The method of claim 1 wherein said tumor is a mammary tumor.

4. The method of claim 1 wherein said nonapeptide is administered at a daily parenteral dose of between 1 and 200 µg/kg.

5. The method of claim 4 wherein said parenteral dose is administered as solution in 0.9% of saline.

6. The method of claim 1 wherein said nonapeptide is administered at a daily oral dose of between 2 and 500 µg/kg.

7. The method of claim 1 wherein said tumor is a DMBA-inducible tumor.

* * * * *